United States Patent
Nalagatla et al.

(10) Patent No.: US 11,744,585 B2
(45) Date of Patent: Sep. 5, 2023

(54) CARTRIDGE RECEIVING JAW FOR SURGICAL STAPLER AND ASSOCIATED METHOD OF MANUFACTURE WITH STAMPING

(71) Applicant: Cilag GmbH International, Zug (CH)

(72) Inventors: Anil K. Nalagatla, Mason, OH (US); Frederick E. Shelton, IV, Hillsboro, OH (US); Chester O. Baxter, III, Loveland, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 181 days.

(21) Appl. No.: 17/331,917

(22) Filed: May 27, 2021

(65) Prior Publication Data

US 2021/0346019 A1  Nov. 11, 2021

Related U.S. Application Data

(63) Continuation of application No. 16/236,688, filed on Dec. 31, 2018, now Pat. No. 11,134,941.

(51) Int. Cl.
*A61B 17/072* (2006.01)
*B21K 5/12* (2006.01)
*A61B 17/00* (2006.01)

(52) U.S. Cl.
CPC .............. *A61B 17/072* (2013.01); *B21K 5/12* (2013.01); *A61B 2017/00526* (2013.01); *A61B 2017/07264* (2013.01); *A61B 2017/07271* (2013.01); *A61B 2017/07278* (2013.01); *A61B 2017/07285* (2013.01)

(58) Field of Classification Search
CPC .................................. A61B 17/072; B21K 5/12
See application file for complete search history.

(56) References Cited

U.S. PATENT DOCUMENTS

| | | | |
|---|---|---|---|
| 5,163,945 | A | 11/1992 | Ortiz et al. |
| 5,205,459 | A | 4/1993 | Brinkerhoff et al. |
| 5,271,544 | A | 12/1993 | Fox et al. |

(Continued)

FOREIGN PATENT DOCUMENTS

WO  WO 2011/028196 A2  3/2011

OTHER PUBLICATIONS

Marini, Daniele, David Cunningham, and Jonathan R. Corney. "Near net shape manufacturing of metal: a review of approaches and their evolutions." *Proceedings of the institution of mechanical engineers, Part B: journal of engineering manufacture* 232.4 (2018): 650-669.

(Continued)

*Primary Examiner* — Nathaniel C Chukwurah
(74) *Attorney, Agent, or Firm* — Frost Brown Todd LLP

(57) ABSTRACT

A method is used to manufacture a lower jaw of an end effector of a surgical instrument. The method includes providing a lower jaw that includes a U-shaped body portion. The U-shaped body portion includes a bottom wall interposed between first and second opposing side walls. The method also includes forming at least one feature into at least one of the first and second side walls, wherein the at least one feature has a near net shape. The method also includes subsequently machining the at least one feature to have a machined shape.

20 Claims, 15 Drawing Sheets

(56) References Cited

U.S. PATENT DOCUMENTS

| | | |
|---|---|---|
| 5,275,322 A | 1/1994 | Brinkerhoff et al. |
| 5,285,945 A | 2/1994 | Brinkerhoff et al. |
| 5,292,053 A | 3/1994 | Bilotti et al. |
| 5,333,773 A | 8/1994 | Main et al. |
| 5,342,373 A | 8/1994 | Stefanchik et al. |
| 5,350,104 A | 9/1994 | Main et al. |
| 5,403,312 A | 4/1995 | Yates et al. |
| 5,431,668 A | 7/1995 | Burbank, III et al. |
| 5,445,167 A | 8/1995 | Yoon et al. |
| 5,533,661 A | 7/1996 | Main et al. |
| 5,601,573 A | 2/1997 | Fogelberg et al. |
| 5,951,574 A | 9/1999 | Stefanchik et al. |
| 6,988,650 B2 | 1/2006 | Schwemberger et al. |
| 7,000,818 B2 | 2/2006 | Shelton, IV et al. |
| 7,134,587 B2 | 11/2006 | Schwemberger et al. |
| 7,147,140 B2 | 12/2006 | Wukusick et al. |
| 7,204,404 B2 | 4/2007 | Nguyen et al. |
| 7,207,472 B2 | 4/2007 | Wukusick et al. |
| 7,261,724 B2 | 8/2007 | Molitor et al. |
| 7,380,696 B2 | 6/2008 | Shelton, IV et al. |
| 7,422,139 B2 | 9/2008 | Shelton, IV et al. |
| 7,464,849 B2 | 12/2008 | Shelton, IV et al. |
| 7,670,334 B2 | 3/2010 | Hueil et al. |
| 7,686,820 B2 | 3/2010 | Huitema et al. |
| 7,699,860 B2 | 4/2010 | Huitema et al. |
| 7,731,724 B2 | 6/2010 | Huitema et al. |
| 7,753,245 B2 | 7/2010 | Boudreaux et al. |
| 7,845,537 B2 | 12/2010 | Shelton, IV et al. |
| 7,980,443 B2 | 7/2011 | Scheib et al. |
| 8,038,686 B2 | 10/2011 | Huitema et al. |
| 8,210,411 B2 | 7/2012 | Yates et al. |
| 8,220,688 B2 | 7/2012 | Laurent et al. |
| 8,262,679 B2 | 9/2012 | Nguyen |
| 8,308,040 B2 | 11/2012 | Huang et al. |
| 8,393,514 B2 | 3/2013 | Shelton, IV et al. |
| 8,408,439 B2 | 4/2013 | Huang et al. |
| 8,453,914 B2 | 6/2013 | Laurent et al. |
| 8,561,870 B2 | 10/2013 | Baxter, III et al. |
| 8,608,045 B2 | 12/2013 | Smith et al. |
| 8,733,613 B2 | 5/2014 | Huitema et al. |
| 8,910,847 B2 | 12/2014 | Nalagatla et al. |
| 9,072,535 B2 | 7/2015 | Shelton, IV et al. |
| 9,101,358 B2 | 8/2015 | Kerr et al. |
| 9,186,142 B2 * | 11/2015 | Fanelli ............ A61B 17/07207 |
| 9,345,481 B2 | 5/2016 | Hall et al. |
| 9,517,065 B2 | 12/2016 | Simms et al. |
| 9,713,469 B2 | 7/2017 | Leimbach et al. |
| 9,717,497 B2 | 8/2017 | Zerkle et al. |
| 9,795,379 B2 | 10/2017 | Leimbach et al. |
| 9,808,248 B2 | 11/2017 | Hoffman |
| 9,839,421 B2 | 12/2017 | Zerkle et al. |
| 9,867,615 B2 | 1/2018 | Fanelli et al. |
| 9,907,552 B2 | 3/2018 | Measamer et al. |
| 9,936,949 B2 | 4/2018 | Measamer et al. |
| 10,092,292 B2 | 10/2018 | Boudreaux et al. |
| 11,134,941 B2 | 10/2021 | Nalagatla et al. |
| 2005/0139636 A1 | 6/2005 | Schwemberger et al. |
| 2005/0143759 A1 | 6/2005 | Kelly |
| 2005/0145672 A1 | 7/2005 | Schwemberger et al. |
| 2007/0175955 A1 | 8/2007 | Shelton, IV et al. |
| 2009/0206143 A1 * | 8/2009 | Huitema .......... A61B 17/07292 227/176.1 |
| 2010/0193568 A1 * | 8/2010 | Scheib ................. A61B 17/105 227/176.1 |
| 2014/0239037 A1 * | 8/2014 | Boudreaux ...... A61B 17/07207 227/175.1 |
| 2014/0263552 A1 | 9/2014 | Hall et al. |
| 2015/0083772 A1 | 3/2015 | Miller et al. |
| 2015/0083773 A1 | 3/2015 | Measamer et al. |
| 2015/0083774 A1 | 3/2015 | Measamer et al. |
| 2015/0083775 A1 | 3/2015 | Leimbach et al. |
| 2016/0374672 A1 | 12/2016 | Bear et al. |
| 2017/0027571 A1 | 2/2017 | Nalagatla et al. |
| 2017/0258471 A1 | 9/2017 | DiNardo et al. |
| 2017/0290584 A1 | 10/2017 | Jasemian et al. |
| 2018/0132849 A1 | 5/2018 | Miller et al. |
| 2018/0132853 A1 | 5/2018 | Miller et al. |
| 2018/0310938 A1 | 11/2018 | Kluener et al. |
| 2018/0310939 A1 | 11/2018 | Stager et al. |
| 2018/0368840 A1 | 12/2018 | Shelton, IV et al. |

OTHER PUBLICATIONS

"Where Component Design Functionality and Cost Reduction Converge: Cold Formed Medical Devices vs. Traditional Manufacturing Techniques", Medical Design Brief, May 7, 2014 (May 7, 2014), Retrieved from the Internet on Apr. 27, 2021: https://dev.rodpub.com//uploads/3623whitepapermwlscoldformedmedicaldevices.pdf.

Extended European Search Report dated Apr. 1, 2020, for Application No. 19220072.3, 13 pages.

International Search Report and Written Opinion dated Mar. 31, 2020, for International Application No. PCT/IB2019/061248, 18 pages.

* cited by examiner

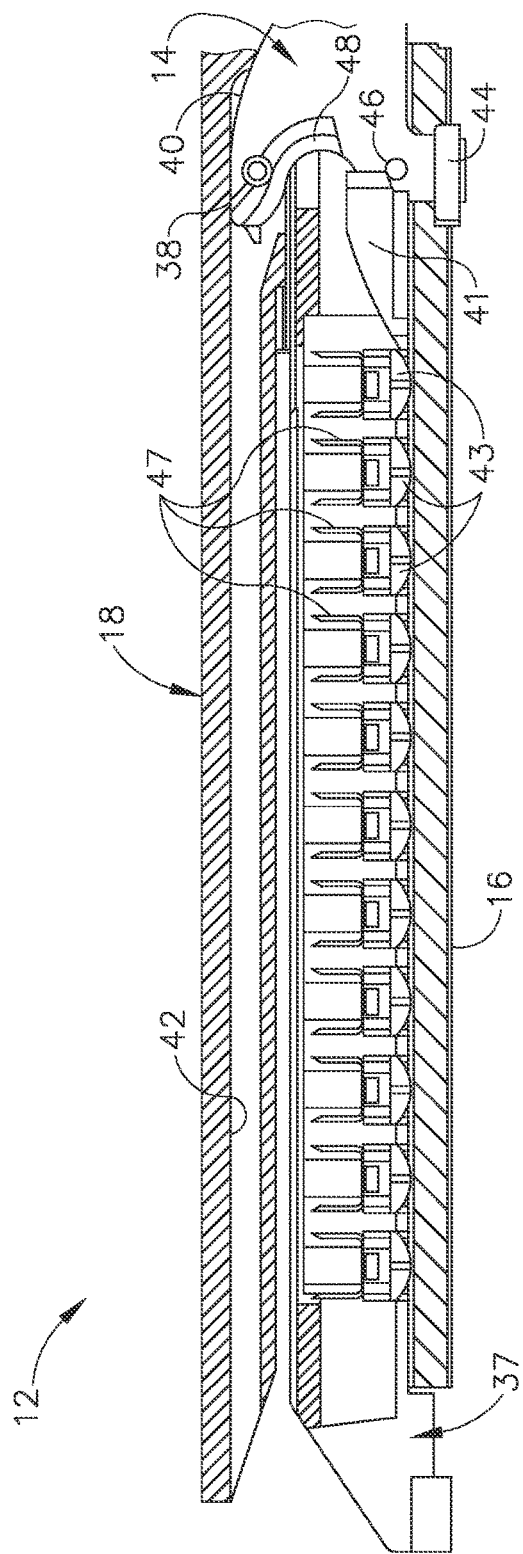
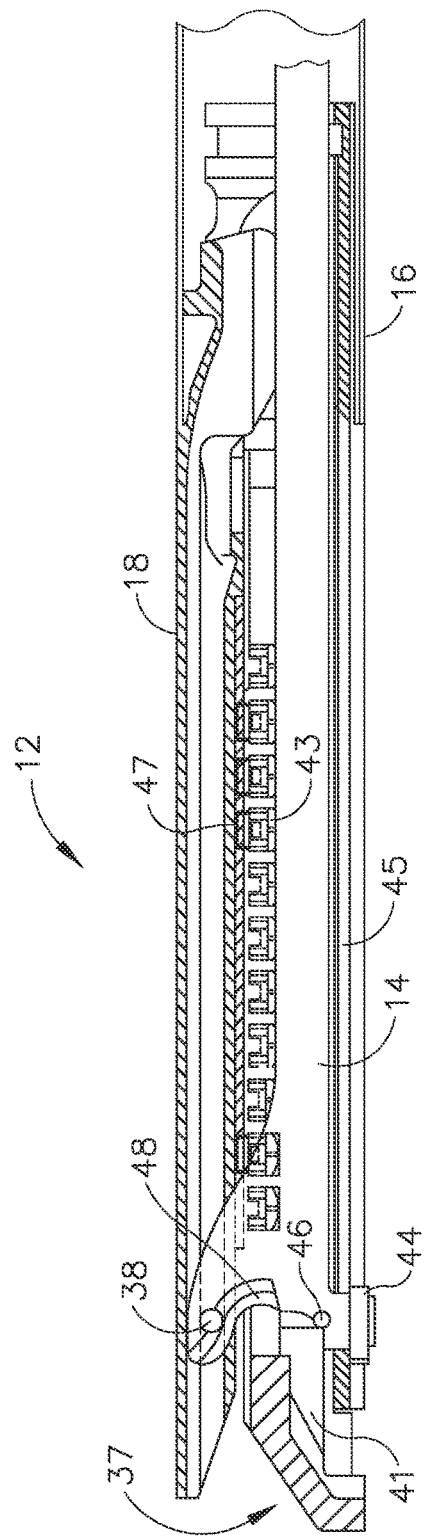
FIG. 4A
FIG. 4B

CARTRIDGE RECEIVING JAW FOR SURGICAL STAPLER AND ASSOCIATED METHOD OF MANUFACTURE WITH STAMPING

This application is a continuation of U.S. patent application Ser. No. 16/236,688, entitled "Cartridge Receiving Jaw for Surgical Stapler and Associated Method of Manufacturing with Stamping," filed Dec. 31, 2018.

BACKGROUND

Endoscopic surgical instruments may include a shaft between the end effector and a handle portion, which is manipulated by the clinician. Such a shaft may enable insertion through a trocar to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,380,696, entitled "Articulating Surgical Stapling Instrument Incorporating a Two-Piece E-Beam Firing Mechanism," issued Jun. 3, 2008; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents and U.S. Patent Publications is incorporated by reference herein.

Surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 4A depicts a side cross-sectional view of the end effector of FIG. 3, taken along line 4-4 of FIG. 3, with the firing beam in a proximal position;

FIG. 4B depicts a side cross-sectional view of the end effector of FIG. 3, taken along line 4-4 of FIG. 3, with the firing beam in a distal position;

Figure 1:
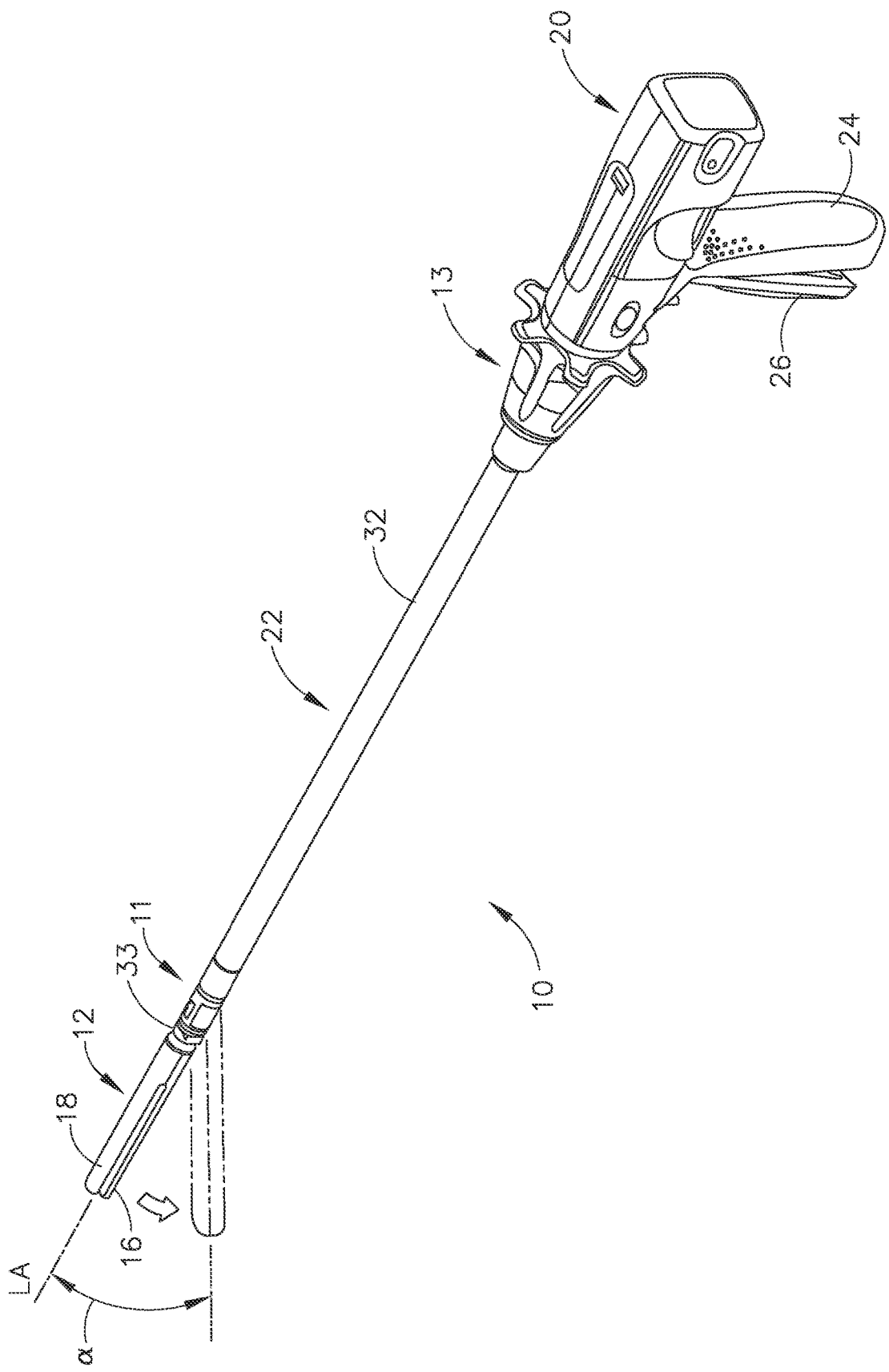
FIG. 1 depicts a perspective view of a first exemplary surgical stapling instrument.
Figure 2:
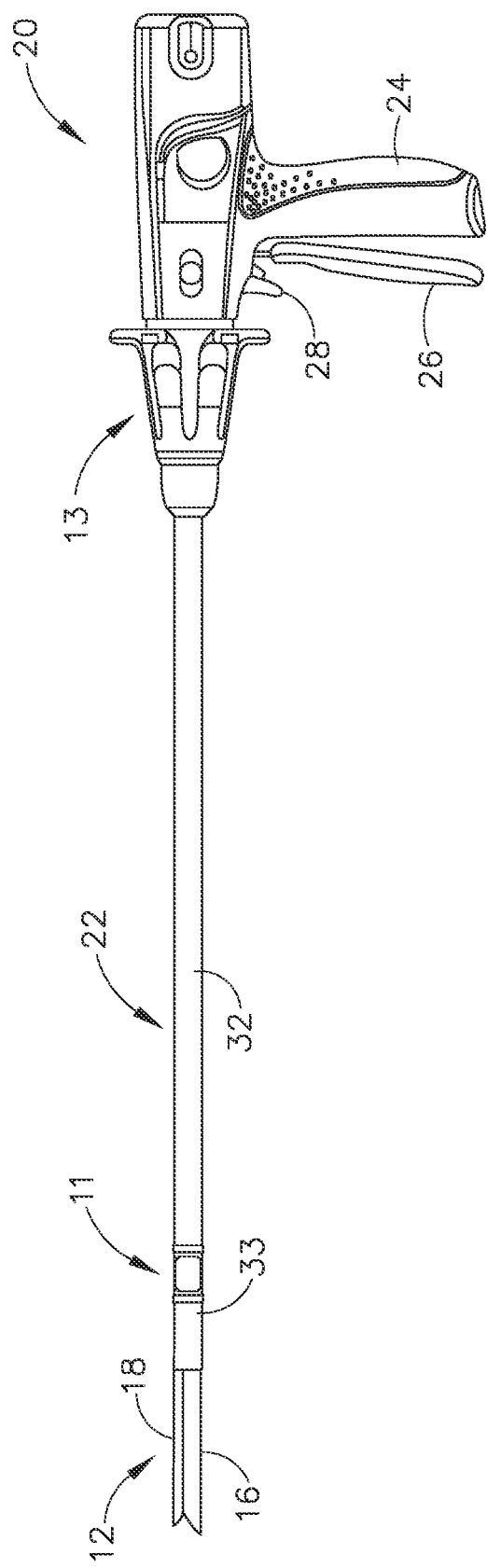
FIG. 2 depicts a side view of the instrument of FIG. 1 with a first exemplary end effector.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

In addition, the terms "first" and "second" are used herein to distinguish one or more portions of the surgical instrument. For example, a first assembly and a second assembly may be alternatively and respectively described as a second assembly and a first assembly. The terms "first" and "second" and other numerical designations are merely exemplary of such terminology and are not intended to unnecessarily limit the invention described herein.

I. FIRST EXEMPLARY SURGICAL INSTRUMENT HAVING A FIRST EXEMPLARY END EFFECTOR

FIGS. 1-6 depict a first exemplary surgical stapling and severing instrument (10) that is sized for insertion through a trocar cannula or an incision (e.g., thoracotomy, etc.) to a surgical site in a patient for performing a surgical procedure. Instrument (10) of the present example includes a handle portion (20) connected to a shaft (22), which distally terminates in an articulation joint (11), which is further coupled with a first exemplary end effector (12). Shaft (22) may be constructed in accordance with at least some of the teachings of U.S. Pat. No. 9,795,379, entitled "Surgical Instrument with Multi-Diameter Shaft," issued Oct. 24, 2017, the disclosure of which is incorporated by reference herein.

Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (a). Articulation joint (11) and/or articulation control (13) may be constructed and operable in accordance with at least some of the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein; and/or U.S. Pat. No. 9,795,379, the disclosure of which is incorporated by reference herein.

End effector (12) of the present example includes a lower jaw (16) and a pivotable anvil (18). Lower jaw (16) may be constructed in accordance with at least some of the teachings of U.S. Pat. No. 9,808,248, entitled "Installation Features for Surgical Instrument End Effector Cartridge," issued Nov. 7, 2017, the disclosure of which is incorporated by reference herein. Anvil (18) may be constructed in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pat. No. 9,839,421, entitled "Jaw Closure Feature for End Effector of Surgical Instrument," issued Dec. 12, 2017, the disclosure of which is incorporated by reference herein; and/or U.S. Pub. No. 2014/0239037, entitled "Staple Forming Features for Surgical Stapling Instrument," published on Aug. 28, 2014, now issued as U.S. Pat. No. 10,092,292 on Oct. 9, 2018, the disclosure of which is incorporated by reference herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33). Handle portion (20) also includes a firing trigger (28) (shown in FIG. 2). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below.

FIGS. 3-6 depict end effector (12) employing an E-beam form of firing beam (14). As best seen in FIGS. 4A-4B, firing beam (14) includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Firing beam (14) and/or associated lockout features may be constructed and operable in accordance with at least some of the teachings of U.S. Pat. No. 9,717,497, entitled "Lockout Feature for Movable Cutting Member of Surgical Instrument," issued Aug. 1, 2017, the disclosure of which is incorporated by reference herein.

Figure 3:
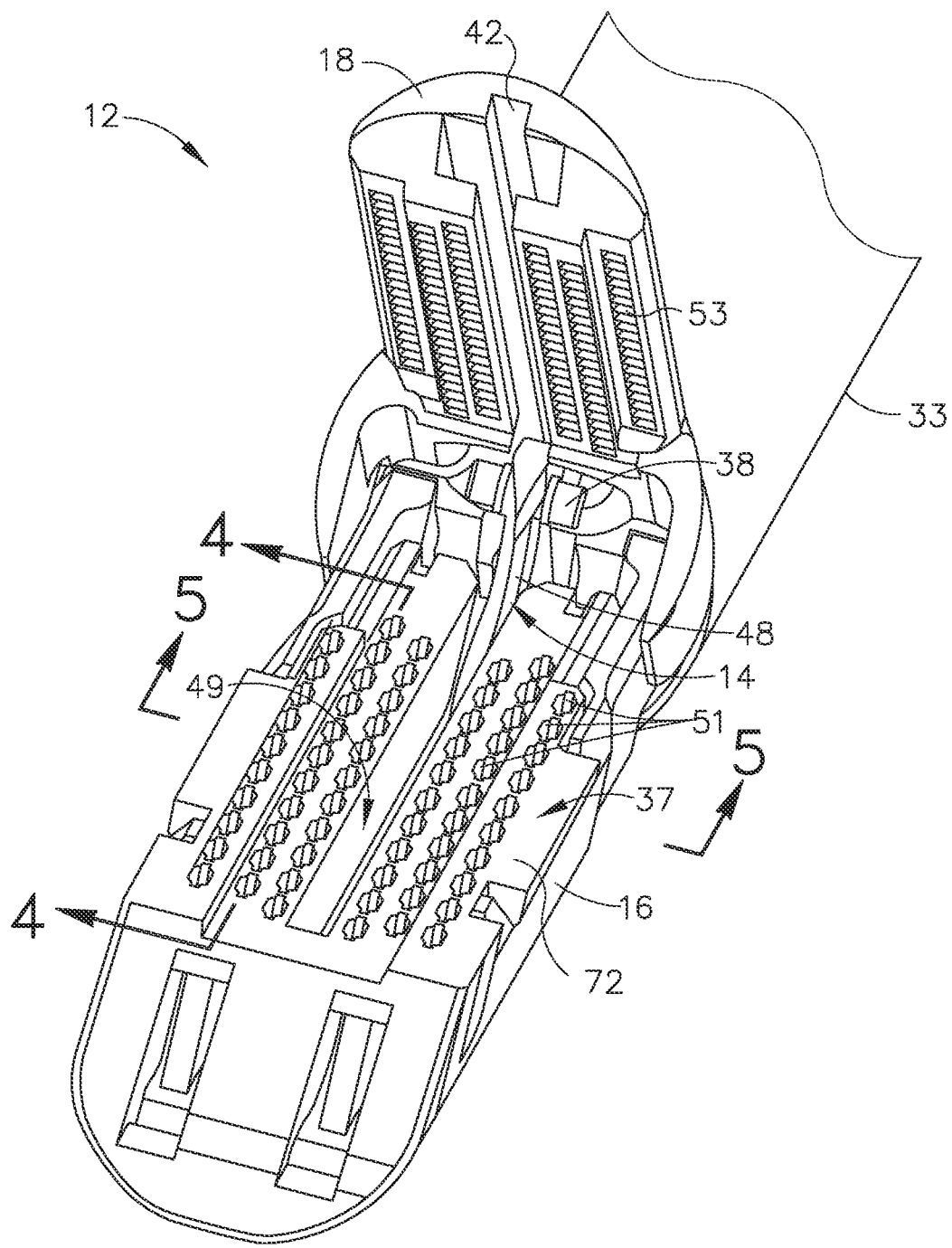
FIG. 3 depicts a perspective view of the end effector of the instrument of FIG. 1 in an open configuration.
Figure 5:
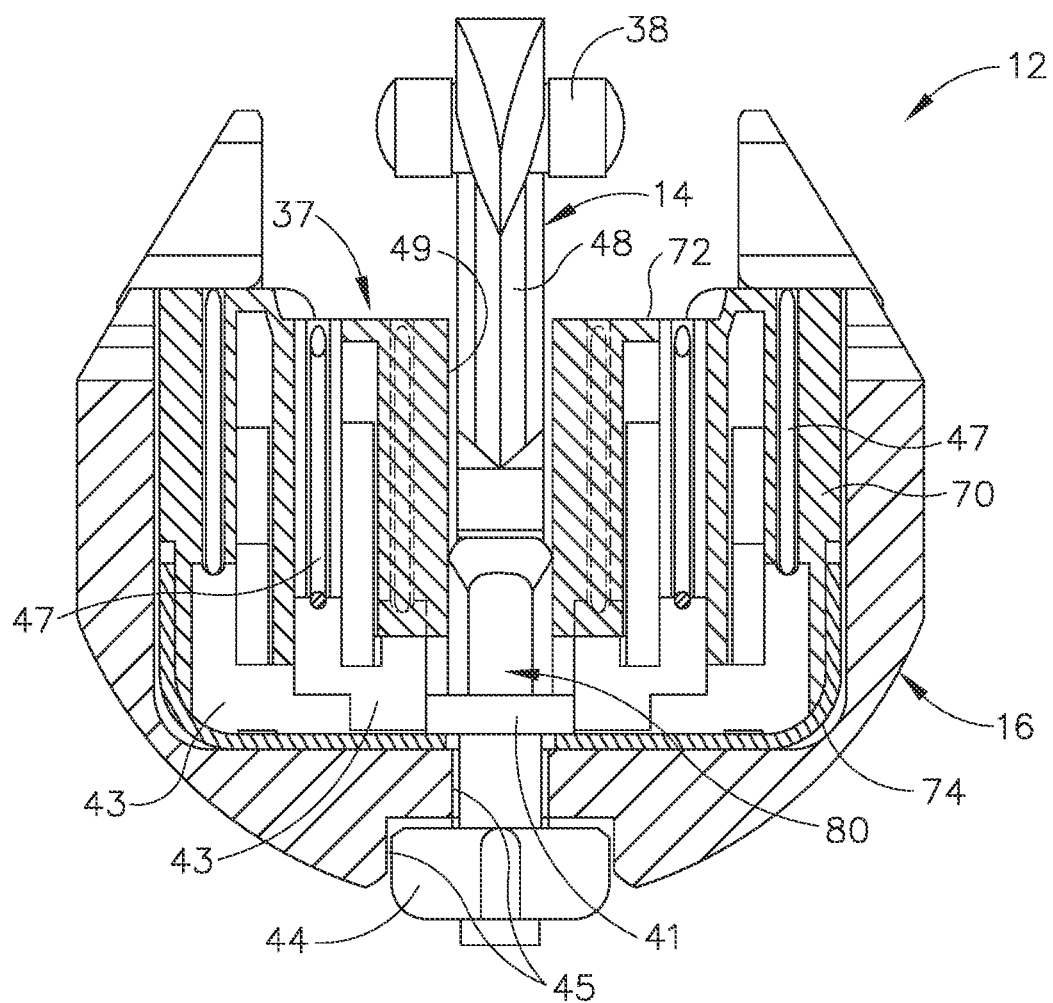
FIG. 5 depicts an end cross-sectional view of the end effector of FIG. 3, taken along line 5-5 of FIG. 3.
Figure 6:
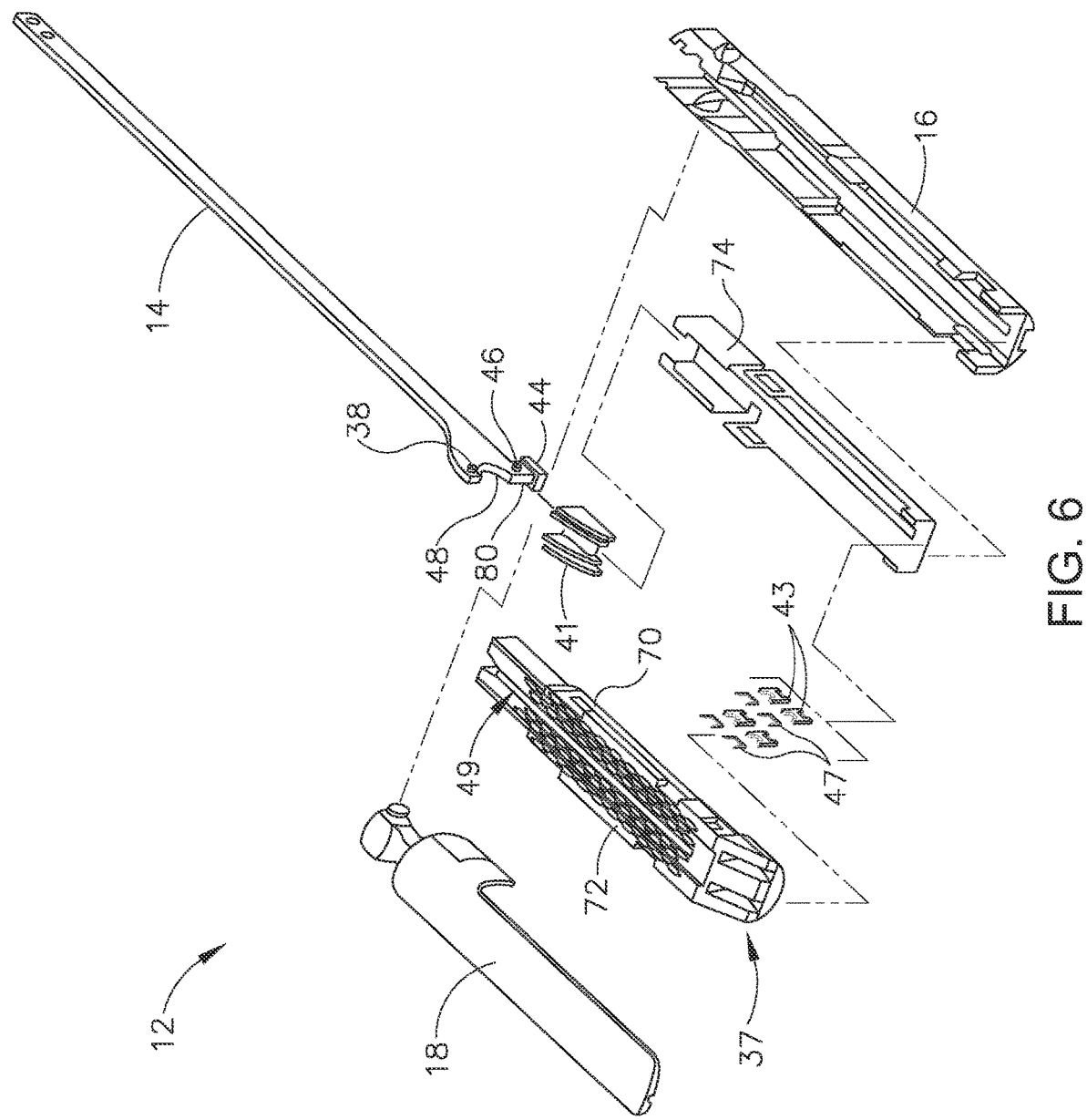
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). As also best seen in FIG. 3, three rows of staple apertures (51) are formed through upper deck (72) on one side of vertical slot (49), with another set of three rows of staple apertures (51) being formed through upper deck (72) on the other side of vertical slot (49). As shown in FIGS. 4A-6, a wedge sled (41) and a plurality of staple drivers (43) are captured between cartridge body (70) and cartridge tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). Each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37). Staple cartridge (37) may be constructed and operable in accordance with at least some of the teachings of U.S. Pat. No. 9,517,065, the disclosure of which is incorporated by reference herein; and/or U.S. Pat. No. 9,808,248, the disclosure of which is incorporated by reference herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) is located at the distal end of firing beam (14) and pushes wedge sled (41) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43), which in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. Staple forming pockets (53) are intentionally omitted from the view in FIGS. 4A-4B; but are shown in FIG. 3. Anvil (18) is intentionally omitted from the view in FIG. 5. In some versions, anvil (18) pivots about an axis that is defined by a pin (or similar feature) that slides along an elongate slot or channel as anvil (18) moves toward lower jaw (16). In such versions, the pivot axis translates along the path defined by the slot or channel while anvil (18) simultaneously pivots about that axis.

Instrument (10) may otherwise be configured and operable in accordance with any of the teachings of any of the patent references cited herein. Additional exemplary modifications that may be provided for instrument (10) will be described in greater detail below. The below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. EXEMPLARY LOWER JAWS AND METHODS OF MANUFACTURE

In some conventional manufacturing processes, lower jaw (16) of instrument (10) may be machined from a single solid block of material (e.g. metal). As a result, this machining of lower jaw (16) may be time consuming and expensive, both of which are undesirable. Conventional machining techniques, being reductive in nature, may also be considered as being inefficient since they may create waste in the material that is removed from the single solid block of material. Additionally, in some instances, considerable machining may impart undesirable stresses into lower jaw (16). As a result, it is desirable to manufacture lower jaw (16) using a faster, more efficient, and more cost-effective process or system of processes to further enhance lower jaw (16). Additionally, it may be desirable that specific portions and features of lower jaw (16) have tight tolerances to aid in the use of instrument (10), while other specific portions and features of lower jaw (16) may have looser tolerances where the precise dimensions are of lesser significance. As such, it is desirable to manufacture an exemplary lower jaw (210, 310) that is efficient, cost effective, and sufficiently robust to interchangeably function with end effector (12) of instrument (10) described above.

As described below, lower jaw (210, 310) may be used in place of lower jaw (16) of instrument (10). Similar to the operation of instrument (10), where anvil (18) pivots relative to lower jaw (16), anvil (18) pivots relative to lower j aw (210, 310). As such, anvil (18) and lower jaw (210, 310) may clamp tissue similarly to the clamping performed by anvil (18) and lower jaw (16) shown in FIG. 1. Similar to lower jaw (16), lower jaw (210, 310) is also configured to receive a staple cartridge, similar to staple cartridge (37) shown in FIG. 3. Additional details of lower jaw (210, 310) are described below with reference to the following figures.

A. Exemplary Lower Jaw Blank

FIGS. 7-12 show an exemplary lower jaw blank (110) that is configured to be transformed into a lower jaw (210, 310) shown in FIGS. 13-19B and FIGS. 20A-20B respectively, through one or more manufacturing processes as described below. Lower jaw (210, 310) is similar to lower jaw (16) of end effector (12), with notable differences indicated below. As previously indicated, instrument (10) includes a body (shown as handle portion (20)), shaft (22) extending from the body, and end effector (12) in communication with shaft (22). End effector (12) is operable to compress, staple, and cut tissue. Lower jaw blank (110), once transformed into lower jaw (210, 310) is configured to be used in place of another lower jaw (e.g. lower jaw (16)) to form a portion of end effector (12).

Figure 7:
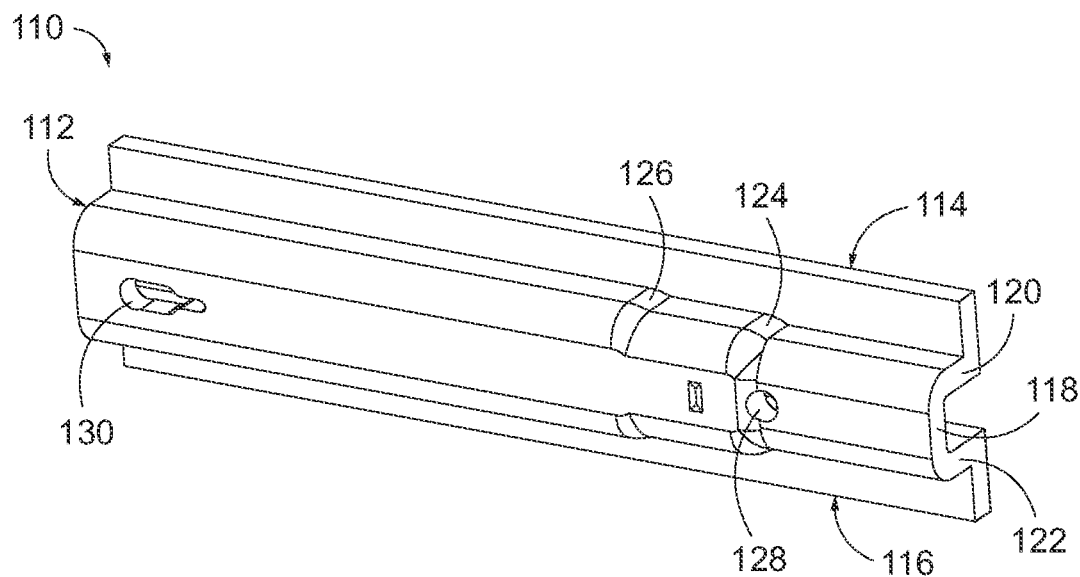
FIG. 7 depicts a bottom perspective view of an exemplary lower jaw blank after being formed to include a U-shaped body portion and first and second outwardly extending flanges, before being further processed to remove the flanges.
Figure 8:
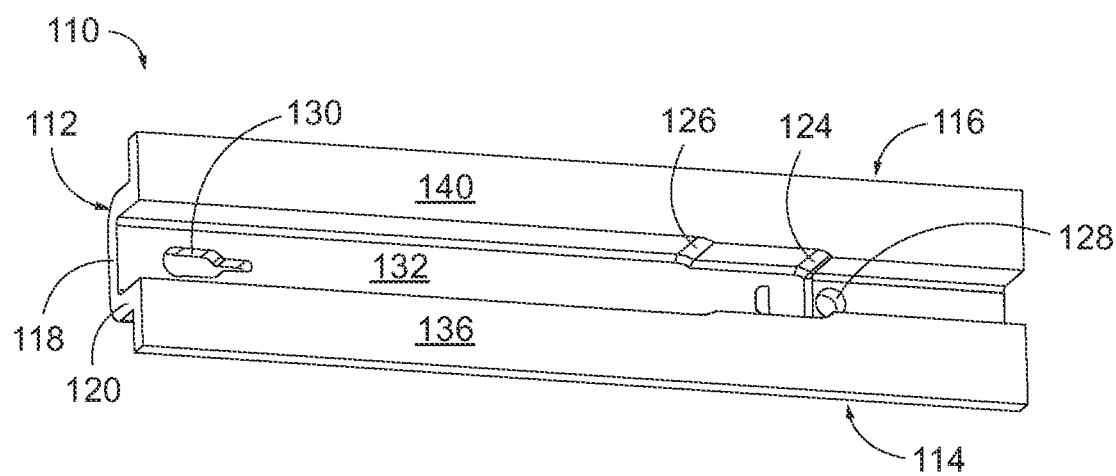
FIG. 8 depicts a top perspective view of lower jaw blank of FIG. 7.
Figure 9:
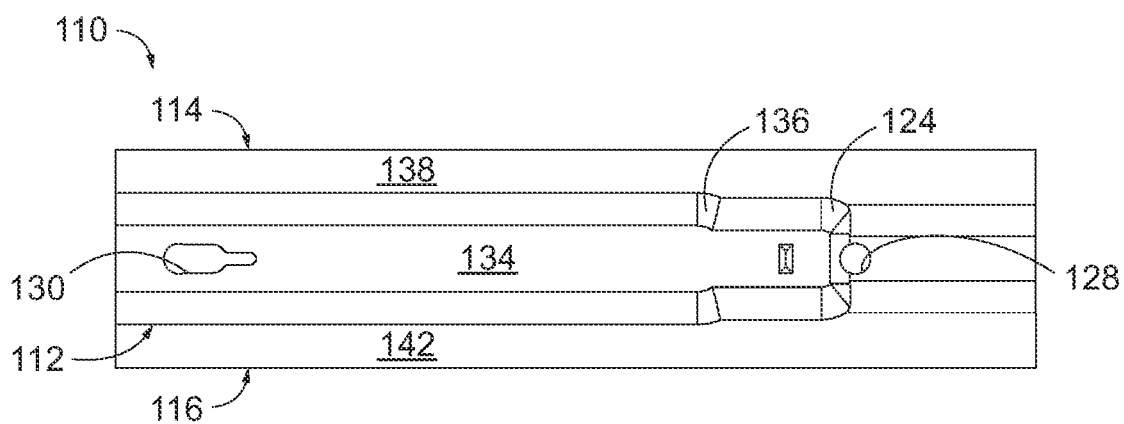
FIG. 9 depicts a bottom view of the lower jaw blank of FIG. 7.
Figure 10:
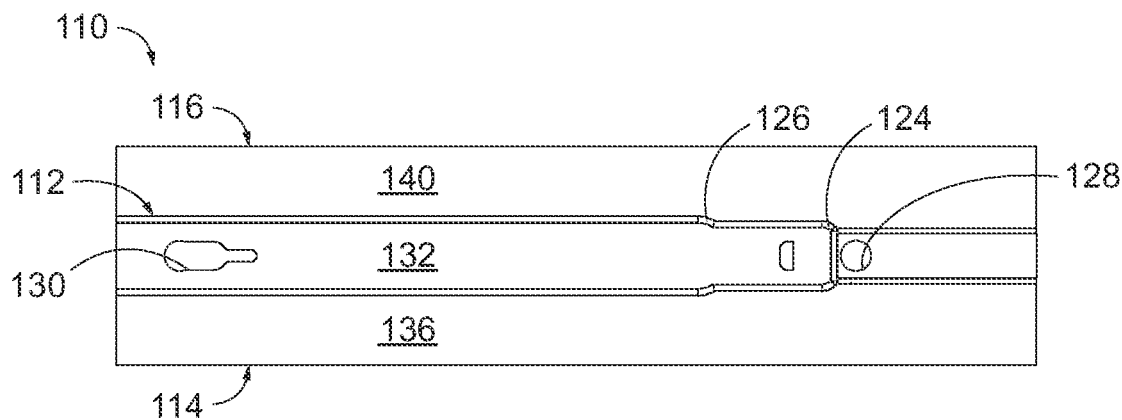
FIG. 10 depicts a top view of the lower jaw blank of FIG. 7.
Figure 11:
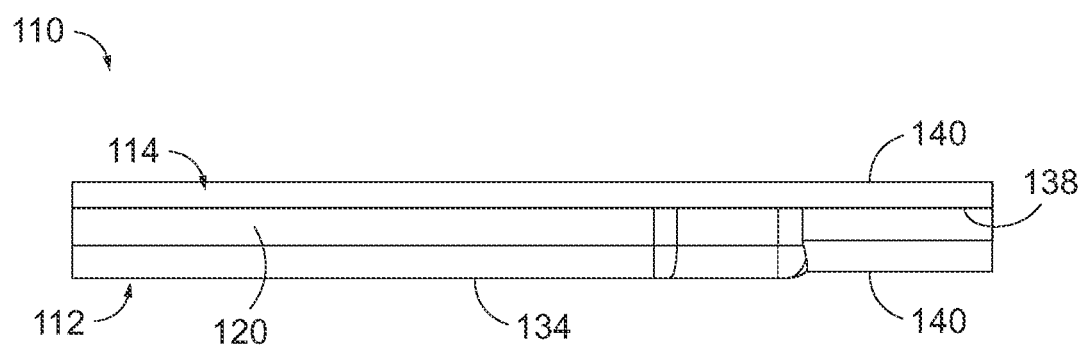
FIG. 11 depicts a left side view of the lower jaw blank of FIG. 7.

As shown in the perspective views of FIGS. 7 and 8, lower jaw blank (110) includes a U-shaped body portion (112) and outwardly extending flanges (114, 116) extending outwardly from U-shaped body portion (112). U-shaped body portion (112) includes a bottom wall (118) interposed between opposing side walls (120, 122). Side walls (120, 122) taper outwardly at outwardly tapering portions (124, 126). As shown, side walls (120, 122) do not include any apertures or cutouts at this manufacturing stage. More specifically, FIGS. 9-12 show respective top, bottom, left side, and distal end views of lower jaw blank (110) prior to any features being formed into opposing side walls (120, 122). As shown, bottom wall (118) includes a proximal aperture (128) and a distal elongated aperture (130) that extend completely through inner and outer surfaces (132, 134) of bottom wall (118).

Figure 12:
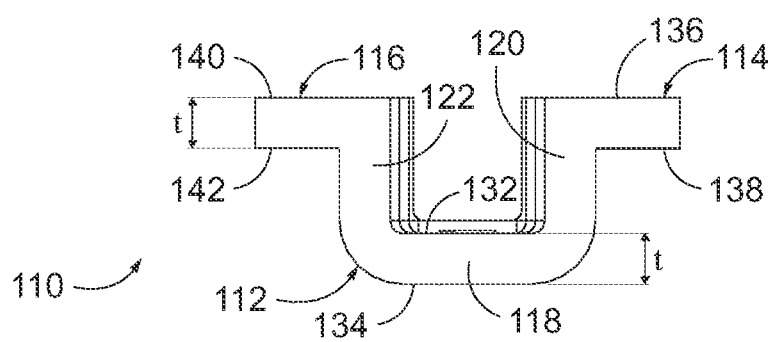
FIG. 12 depicts a distal end view of the lower jaw blank of FIG. 7.
Figure 13:
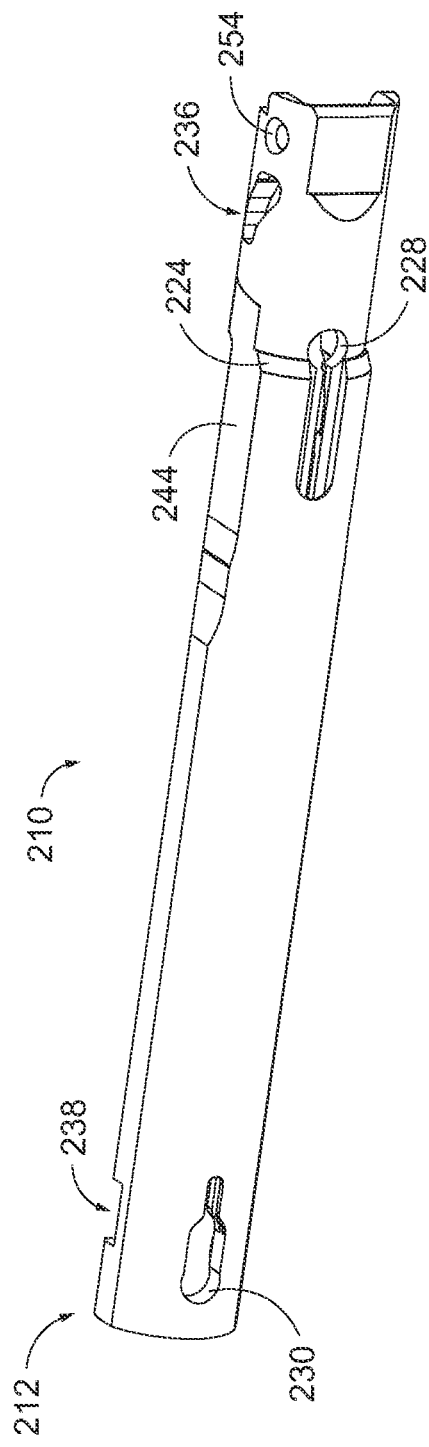
FIG. 13 depicts a bottom perspective view of a lower jaw formed from the lower jaw blank of FIG. 7 after being machined.
Figure 14:
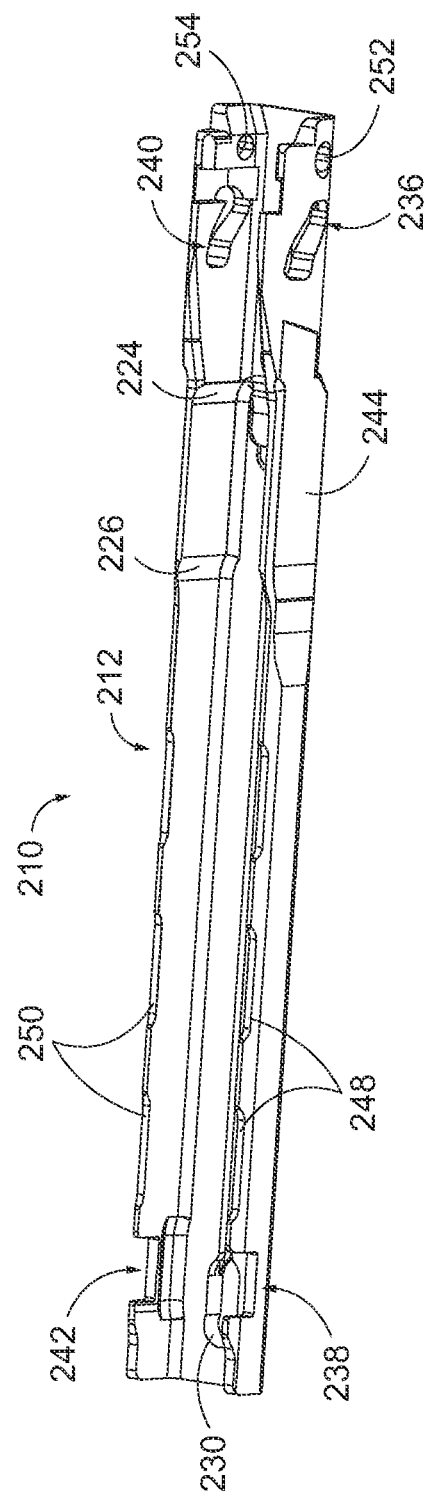
FIG. 14 depicts a top perspective view of the lower jaw of FIG. 13.
Figure 15:
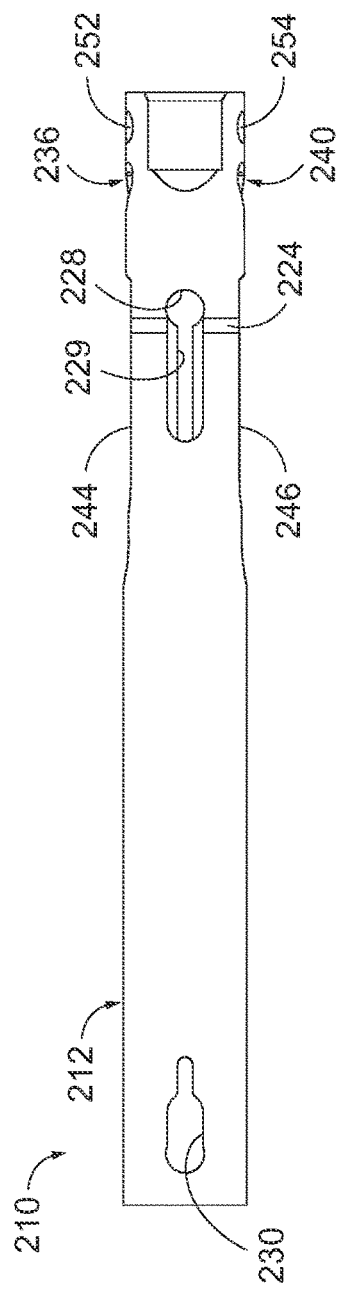
FIG. 15 depicts a bottom view of the lower jaw of FIG. 13.
Figure 16:
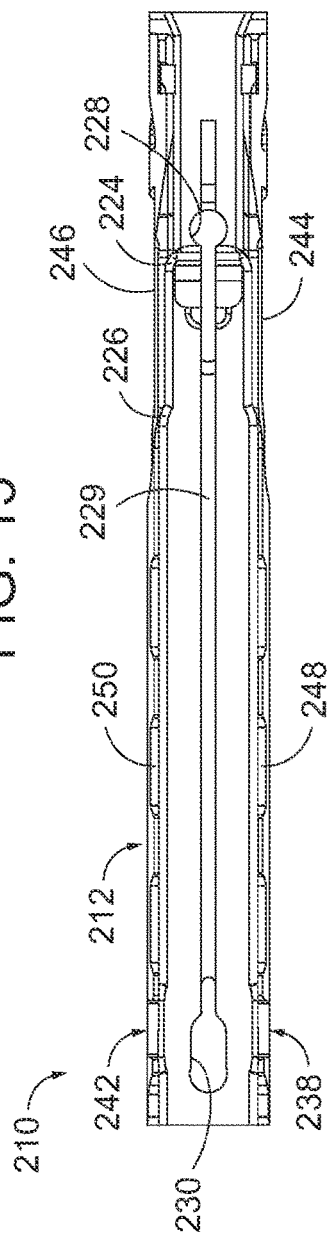
FIG. 16 depicts a top view of the lower jaw of FIG. 13.

As shown in the distal end view of FIG. 12, side walls (120, 122) extend vertically at right angles from bottom wall (118), which is horizontally oriented. However, other angles between bottom wall (118) and side walls (120, 122) are also envisioned. More specifically, outwardly extending flange (114) extends from side wall (120) and includes opposing upper and lower planar surfaces (136, 138) shown in FIG. 12. Similarly, outwardly extending flange (116) extends from side wall (122) and includes opposing upper and lower planar surfaces (140, 142). As shown in FIG. 12, thickness (t) of lower jaw blank (110) is generally constant. However, thickness (t) may vary if desired. One or more stamping operations may be used to impart one or more additional features in bottom wall (118) and side walls (120, 122) as will be described in greater detail below.

While not shown, lower jaw blank (110) may be initially transformed from an initial flat planar sheet into U-shaped body portion (112) and outwardly extending flanges (114, 116) using one or more manufacturing processes (e.g. one or more sequential stamping operations). Instead of or in addition to one or more stamping operations, lower jaw blank (110) may be formed using additive manufacturing, selective laser melting, direct metal laser sintering, and/or metal injection molding. Certain manufacturing processes (stamping, additive manufacturing, selective laser melting, direct metal laser sintering, and/or metal injection molding) may result in looser tolerances than desired. In view of the tight tolerances desired for manufacture of instrument (10), it is desirable to refine at least certain specific portions of lower jaw blank (110) to improve the dimensional accuracy of lower jaw blank (110).

B. First Exemplary Lower Jaw

FIGS. 13-19 show an exemplary lower jaw (210) after at least one manufacturing process is performed to lower jaw blank (110). As shown in the perspective views of FIGS. 13-14, outwardly extending flanges (114, 116) have been removed using at least one manufacturing process (e.g. one or more stamping operations). Lower jaw (210) includes a U-shaped body portion (212) that includes a bottom wall (218) interposed between opposing side walls (220, 222). The inside of U-shaped body portion (212) forms a channel configured to receive a staple cartridge. Side walls (220, 222) taper outwardly at outwardly tapering portions (224, 226). Additionally, bottom wall (218) includes a proximal aperture (228) and a distal elongated aperture (230) that extend completely through inner and outer surfaces (232, 234) of bottom wall (218). Proximal aperture (228) and distal elongated aperture (230) are connected by a longitudinally extending channel (229).

Side walls (220, 222) include one or more apertures and cutouts. As shown in FIGS. 13-14 and 16-17, side wall (220) includes a proximal aperture (236) and a distal cutout (238). Similarly, side wall (222) includes a proximal aperture (240) and a distal cutout (242). One or more manufacturing processes (e.g. one or more stamping operations) may be performed to impart proximal apertures (236, 240) and distal cutouts (238, 242) to the intermediate state of the lower jaw, where the intermediate state occurs at a point in time between lower jaw blank (110) and lower jaw (210)). Additionally, as shown, side walls (220, 222) also include inwardly tapering portions (244, 246), recessed portions (248, 250), and apertures (252, 254).

Figure 17:
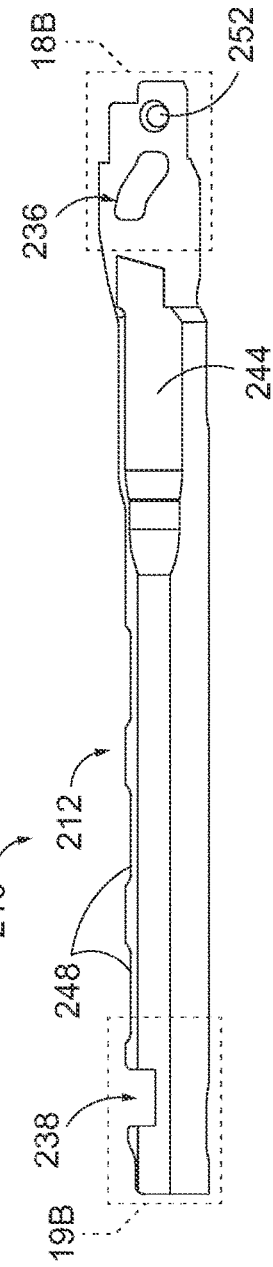
FIG. 17 depicts a left side view of the lower jaw of FIG. 13 including a distal cutout and a proximal aperture.
Figure 18A:
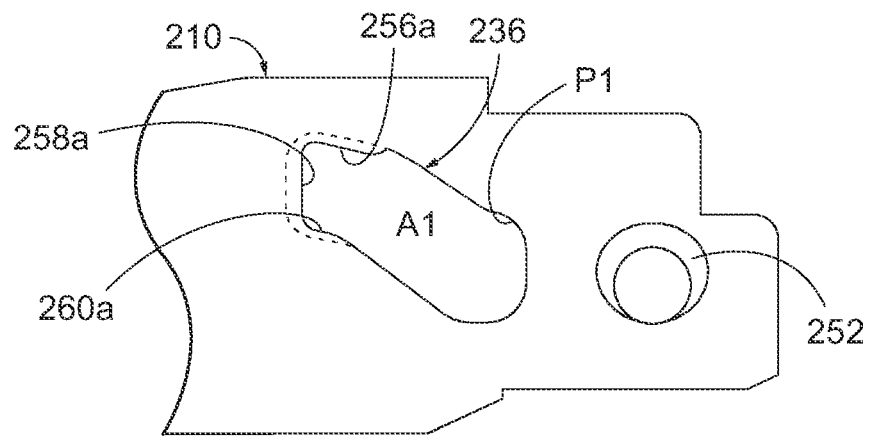
FIG. 18A depicts a detailed view of the proximal aperture similar to FIG. 17 after being formed but prior to being machined.
Figure 18B:
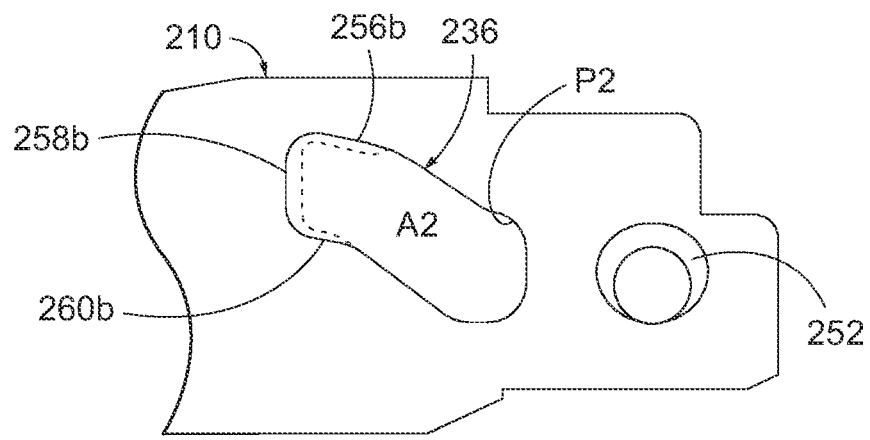
FIG. 18B depicts a detailed view of the proximal aperture of FIG. 17 after being machined.

FIG. 17 shows a left side view of lower jaw (210) including proximal aperture (236) and distal cutout (238), with proximal aperture (240) and distal cutout (242) being mirror images thereof. Proximal aperture (236) is described in detail below; however, the principles and accompanying features apply equally to proximal aperture (240). FIG. 18A shows a detailed view of proximal aperture (236) after being formed but prior to be machined, while FIG. 18B shows a detailed view of proximal aperture (236) of FIG. 17 after having been machined. Proximal aperture (236) is generally kidney shaped. As shown in FIG. 18A, proximal aperture (236) has a near net shape with an initial area (A1) defined by the continuous solid line. As used herein, "near net shape" means that the initial forming operations create an intermediate (near net) shape that is very close to the final (net) shape, which reduces the need and associated cost of significant surface finishing. These initial forming operations may include, for example, stamping, additive manufacturing, selective laser melting, direct metal laser sintering, and/or metal injection molding.

As shown in FIG. 18B, proximal aperture (236) has a machined shape with a machined area (A2) defined by the continuous solid line, with the dashed line denoting the near net shape shown in FIG. 18A. As shown, only distal portions of proximal aperture (236) are machined, such that the remainder of proximal aperture (236) is not machined. As shown in FIG. 18A-18B, only upper, middle, and lower distal surfaces (256a, 258a, 260a) are machined which results in upper, middle, and lower distal surfaces (256b, 258b, 260b) after the machining operation(s). As shown in FIG. 18B, proximal aperture (236) has a machined area (A2) that is greater than initial area (A1), since material is removed from upper, middle, and lower distal surfaces (256a, 258a, 260a) to form upper, middle, and lower distal surfaces (256b, 258b, 260b). However, it is also envisioned that the entire initial perimeter (P1) of the proximal aperture (236) may be machined if desired to produce a machined perimeter (P2). For example, this may be beneficial if tighter tolerances are required for desired operation.

Figure 19A:
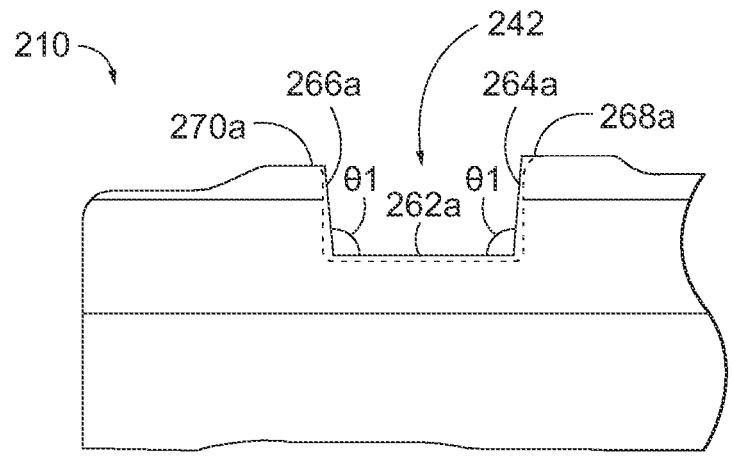
FIG. 19A depicts a detailed view of the distal cutout similar to FIG. 17, after being formed but prior to being machined.
Figure 19B:
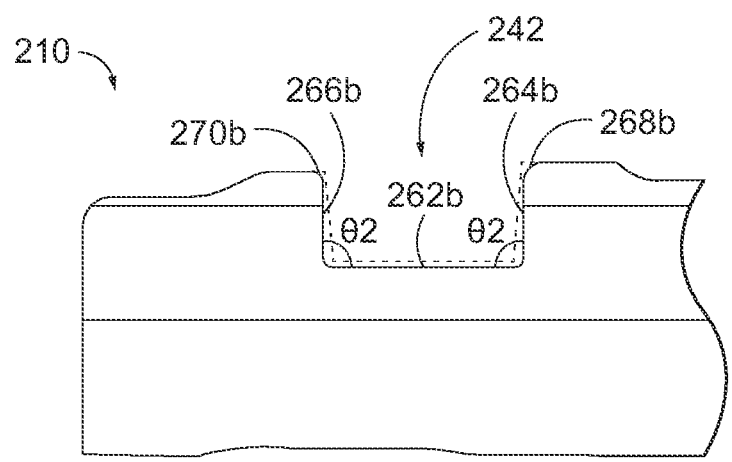
FIG. 19B depicts a detailed view of the distal cutout of FIG. 17 after being machined.

FIGS. 19A-19B show distal cutout (238). More specifically, FIG. 19A shows a detailed view of distal cutout (238) after being formed but prior to be machined, while FIG. 19B shows a detailed view of distal cutout (238) after being machined. Similar to proximal aperture (236, 240), distal cutout (242) is a mirror image of distal cutout (238). As a result, the principles and accompanying features described for distal cutout (238) apply equally to distal cutout (242). As shown in FIGS. 19A-19B, distal cutout (238) includes a bottom wall (262a), a proximal wall (264a), and a distal wall (266a), forming a generally rectangular shape. As shown in FIG. 19A, distal cutout (238) has near net shape with an obtuse interior angle ($\theta 1$). More specifically, near net shapes produce an obtuse angle between bottom and proximal walls (262a, 264a) and an obtuse angle ($\theta 1$) between bottom and distal walls (262a, 266a).

As shown in FIG. 19B, distal cutout (238) has a machined shape with approximately 90-degree interior angles ($\theta 2$). In other words, the near net shape of distal cutout (238) with obtuse interior angles ($\theta 1$) obtained using at least one stamping process, are machined into machined shapes with approximately 90-degree interior angles ($\theta 2$). More specifically, distal cutout (238) is machined to have a 90-degree angle ($\theta 2$) between bottom and proximal walls (262b, 264b) and 90-degree angle ($\theta 2$) between bottom and distal walls (262b, 266b). Additionally, top edges (268a, 270a) of FIG. 19A surrounding distal cutout (242) are machined to top edges (268b, 270b) of FIG. 19B. As shown, the machined shape is the finalized shape, however more manufacturing operations may be performed if desired.

C. Second Exemplary Lower Jaw

Figure 20A:
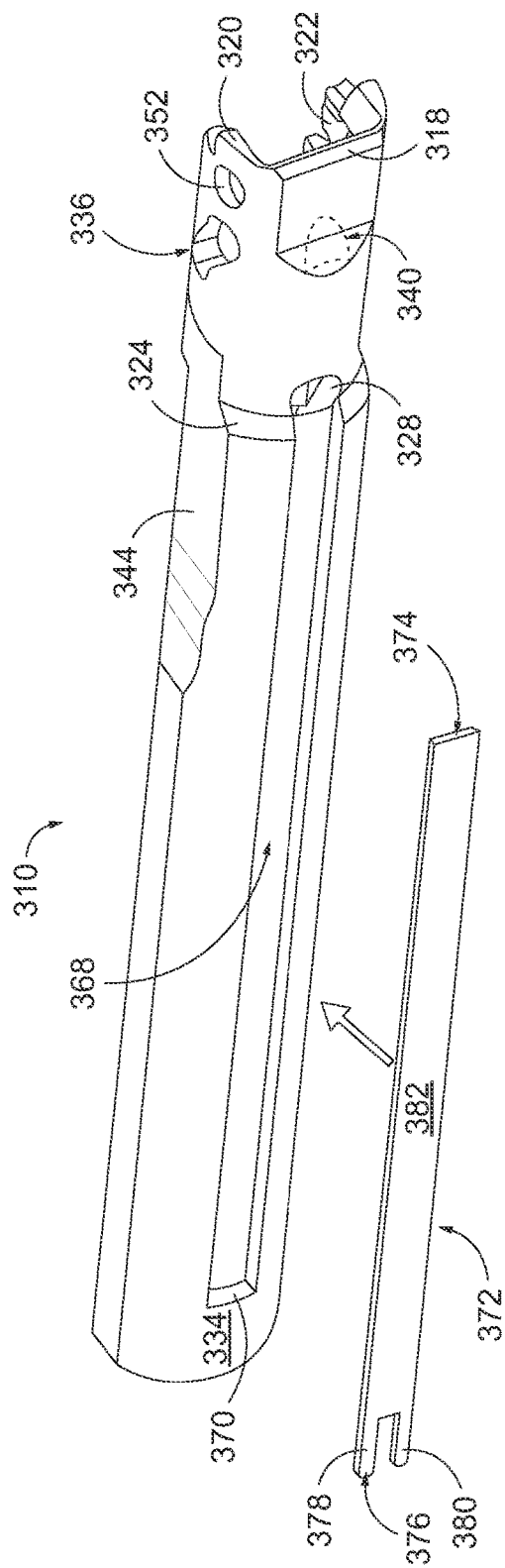
FIG. 20A depicts a top perspective view of a second exemplary lower jaw and a back member prior to being coupled together.
Figure 20B:
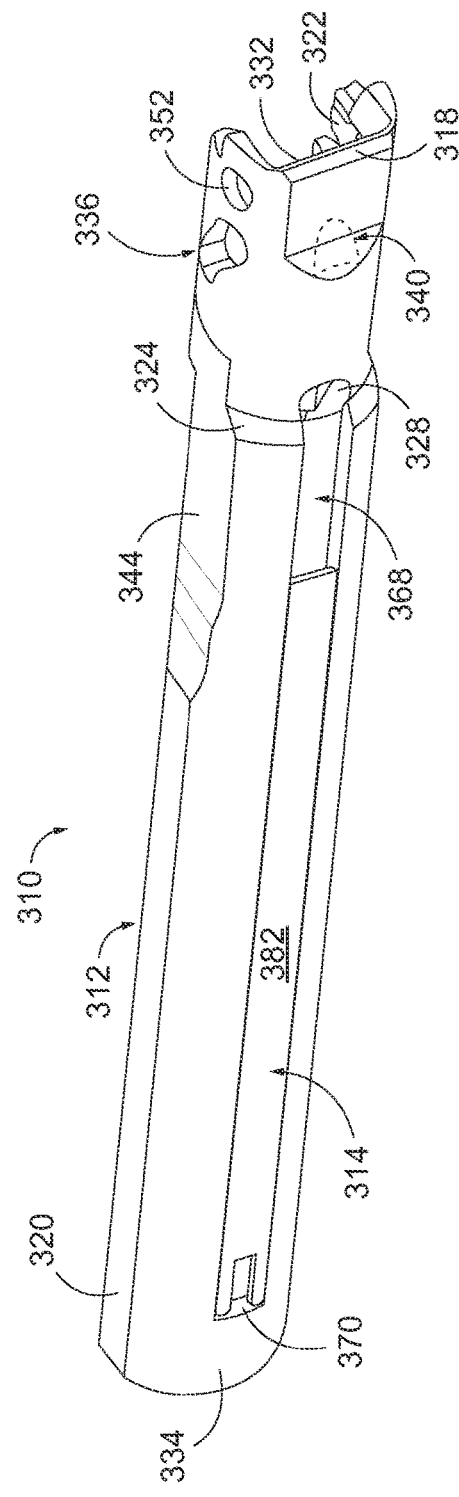
FIG. 20B depicts a top perspective view of the lower jaw and the back member of FIG. 20A, after being coupled together.

FIGS. 20A-20B show a second exemplary lower jaw (310). Lower jaw (310) comprises a U-shaped body portion (312), a bottom wall (318), opposing side walls (320, 322), a tapering portion (324), a proximal aperture (328), inner and outer surfaces (332, 334) of bottom wall (318), proximal apertures (336, 340), an inwardly tapering portion (344), and an aperture (352). Proximal apertures (336, 340) are formed and subsequently machined using a method similar to that described with respect to proximal apertures (236, 240).

As shown in FIGS. 20A-20B, lower jaw (310) does not include distal cutouts, similar to distal cutouts (238, 242) described above with respect to lower jaw (210). However, if desired, distal cutouts may be imparted similar to distal cutouts (238, 242) of lower jaw (210). As shown in FIG. 20A, outer surface (334) of bottom wall (318) includes a recessed portion (368) that extends longitudinally. Recessed portion (368) terminates proximally at proximal aperture (328) and distally at a distal wall (370).

Recessed portion (368) is configured to receive a lower longitudinally extending back member (372) having proximal and distal ends (374, 376). Projections (378, 380) of lower longitudinally extending back member (372) extend distally from distal end (376) of lower longitudinally extending back member (372). Lower longitudinally extending back member (372) is configured to provide additional support for bottom wall (318). Outer surface (382) of lower longitudinally extending back member (372) may extend flush with outer surface (334) of bottom wall (318). Lower longitudinally extending member (372) may be coupled to outer surface (334) of bottom wall (318) before, during, or after machining of the at least one feature (e.g. proximal apertures (336, 340)). For example, lower longitudinally extending back member (372) may be welded to outer surface (334) of bottom wall (318).

D. First Exemplary Method of Manufacture

Figure 21:
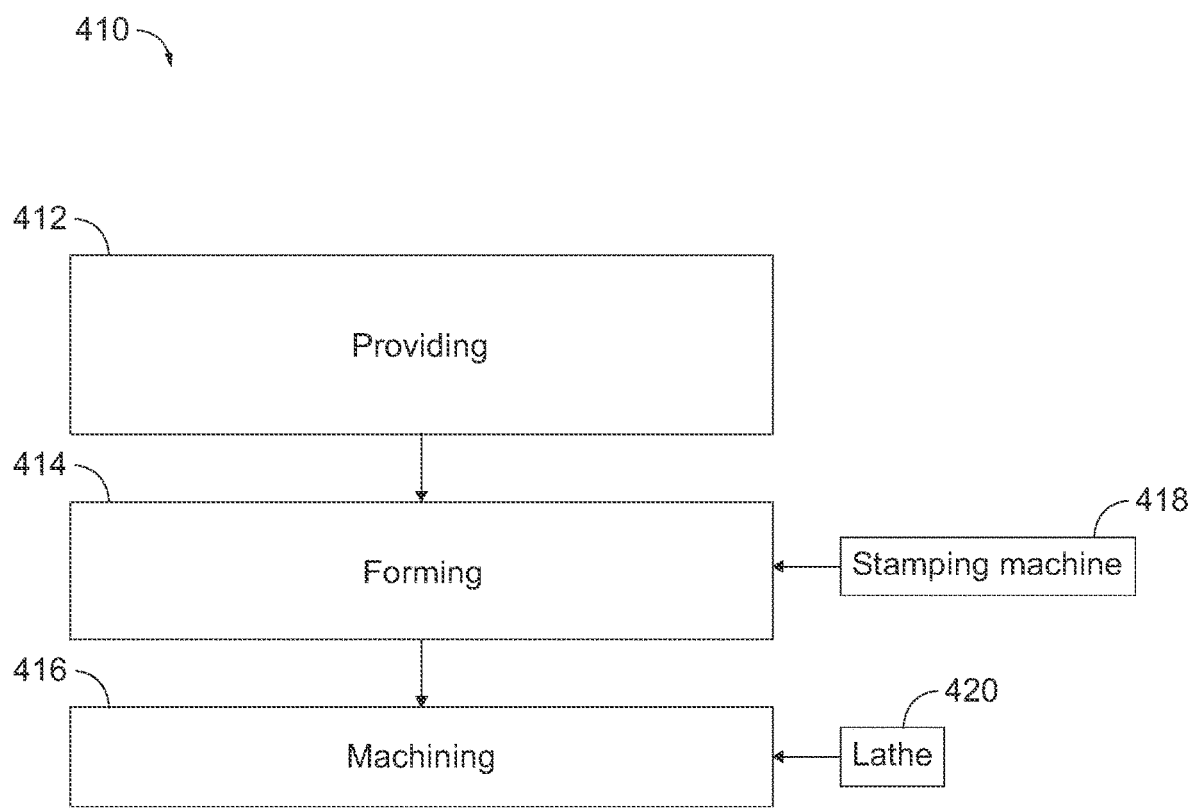
FIG. 21 depicts a first exemplary method of manufacturing a lower jaw.

FIG. 21 shows a method (410) of manufacturing lower jaw (210, 310) of end effector (12) of surgical instrument (10) that includes at least three steps (412, 414, 416). As shown, at step (412), the method includes providing a lower jaw blank (110) that includes U-shaped body portion (112). U-shaped body portion (112) includes bottom wall (118) interposed between opposing side walls (120, 122). As previously described, lower jaw blank (110) may be formed using one or more manufacturing processes (e.g. one or more sequential stamping operations performed by a stamping machine). Instead of or in addition to one or more stamping operations, lower jaw blank (110) may be formed using additive manufacturing, selective laser melting, direct metal laser sintering, and/or metal injection molding.

At step (414), the method also includes forming the at least one feature (e.g. proximal apertures (236, 240, 336) and/or distal cutouts (238, 242)) into at least one of side walls (120, 122). The feature (e.g. proximal apertures (236, 240, 336)) and/or distal cutouts (238, 242)) has a near net shape. The feature (e.g. proximal apertures (236, 240, 336) and/or distal cutouts (238, 242)) may be formed using a variety of manufacturing processes, (e.g. one or more sequential stamping operations performed by a stamping machine (418)). The manufacturing processes used to form the at least one feature (e.g. proximal apertures (236, 240, 336) and/or distal cutouts (238, 242)) into at least one of side walls (120, 122) may be the same or different.

At step (416), the method includes subsequently machining the feature (e.g. proximal apertures (236, 240, 336) and/or distal cutouts (238, 242)) to have a machined shape. If two or more features are imparted, the features may be imparted simultaneously or sequentially. For example, a first feature may be formed in the first side wall through a first manufacturing process, and subsequently a second feature may be formed in the second side wall through a second manufacturing process. Non-machined portions of lower jaw (210, 310) have a first surface finish and machined portions of lower jaw (210, 310) have a second surface finish. The second surface finish is finer than the first surface finish. For example, the second surface finish may be substantially finer than the first surface finish. Step (416) may be performed using a variety of machining tools, for example, using a lathe (420), which may be manually operated or automated.

E. Second Exemplary Method of Manufacture

Figure 22:
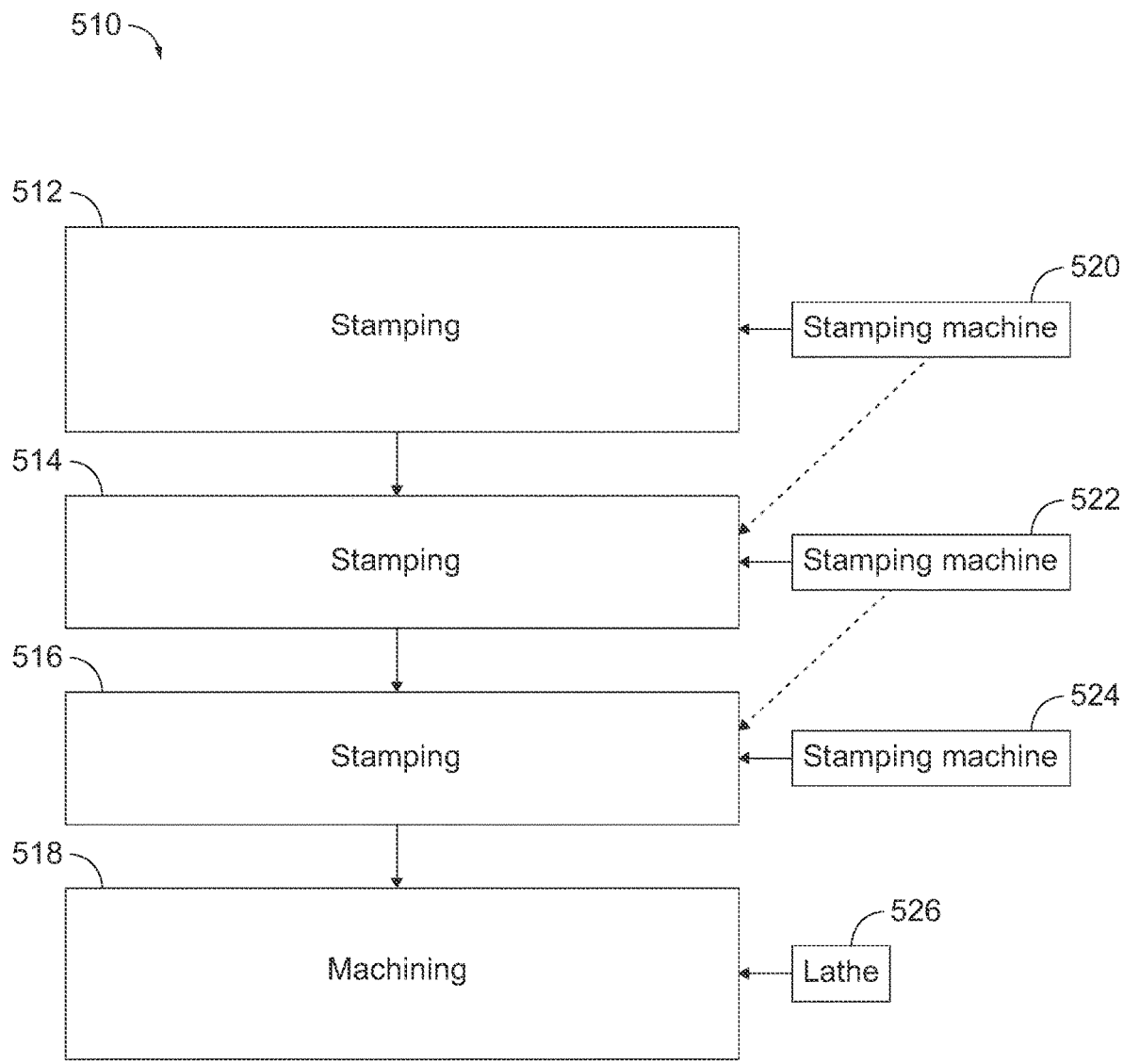
FIG. 22 depicts a second exemplary method of manufacturing a lower jaw.

FIG. 22 shows a method (510) of manufacturing lower jaw (210, 310) of end effector (12) of surgical instrument (10) that includes at least four steps (512, 514, 516, 518). At step (512), the method includes stamping lower jaw blank (110) to include a U-shaped body portion (112). U-shaped body portion (112) of lower jaw blank (110) includes bottom wall (118) and opposing side walls (120, 122). As previously described, U-shaped body portion (112) may be formed using one or more manufacturing processes (e.g. one or more sequential stamping operations performed by a stamping machine (520)). Instead of or in addition to one or more stamping operations, U-shaped body portion (112) may be formed using additive manufacturing, selective laser melting, direct metal laser sintering, and/or metal injection molding.

At step (514), the method also includes stamping proximal aperture (236, 336) of side wall (220, 320). Proximal aperture (236, 336) has a near net shape with first area (A1). One or more sequential stamping operations may be performed by a stamping machine (522), that may be the same or different from stamping machines (520). A variety of other manufacturing processes may be used instead of, or in addition to, stamping.

At step (516), the method also includes stamping side wall (222, 322) to include proximal aperture (240, 340). Proximal aperture (240, 340) has a near net shape with first area (A1). Stamping proximal aperture (240, 340) may happen before, simultaneously with, or after, the stamping of proximal aperture (236, 336). For example, a first feature (e.g. proximal aperture (236, 336)) may be formed in side wall (220, 320) through a first manufacturing process, and subsequently a second feature (e.g. proximal aperture (240, 340)) may be formed in the side wall (222, 322) through a second manufacturing process. The first and second manufacturing processes may be the same or different. One or more sequential stamping operations performed by a stamping machine (524), that may be the same or different from stamping machines (520, 522). A variety of other manufacturing processes may be used instead of or in addition to stamping of proximal aperture (240, 340).

At step (518), the method also includes subsequently machining proximal apertures (236, 240, 336, 340) to have machined shapes with second areas. Second area (A2) is less than first area (A1). As shown, only distal portions (e.g. distal surfaces (256a, 258a, 260a)) of proximal apertures (236, 240, 336, 340) are machined into distal portions (e.g. distal surfaces (256b, 258b, 260b)) such that remainder of proximal apertures (236, 240) are not machined. It is envisioned that the machining of proximal aperture (240) may happen before, simultaneously with, or after the machining of proximal aperture (236). Non-machined portions of lower jaw (210, 310) have a first surface finish and machined portions of lower jaw (210, 310) have a second surface finish. The second surface finish is finer than the first surface finish. For example, the second surface finish may be substantially finer than the first surface finish. Step (518) may be performed using a variety of machining tools, for example, using a lathe (526), which may be manually operated or automated.

While method (510) is described with respect stamping and subsequent machining of proximal apertures (236, 240, 336, 340), these principles apply equally to distal cutouts (238, 242) and other features, where improved tolerances are desired. The exemplary methods (410, 510) using near net shapes reduce the need for costly machining by providing lower jaw (210, 310) already having one or more features already imparted.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of manufacturing a lower jaw of an end effector of a surgical instrument, the method comprising: (a) providing a lower jaw that includes a U-shaped body portion, wherein the U-shaped body portion includes a bottom wall interposed between first and second opposing side walls; (b) forming at least one feature into at least one of the first and second side walls, wherein the at least one feature has a near net shape; and (c) subsequently machining the at least one feature to have a machined shape.

Example 2

The method of Example 1, wherein forming the at least one feature comprises performing at least one stamping process to form the at least one feature after providing the lower jaw.

Example 3

The method of Example 1 or Example 2, wherein forming the at least one feature further comprises forming a first feature in the first side wall through a first manufacturing process, and subsequently forming a second feature in the second side wall through a second manufacturing process.

Example 4

The method of any one or more of Examples 1 through 3, wherein non-machined portions of the lower jaw have a first surface finish and machined portions of the lower jaw have a second surface finish, wherein the second surface finish is finer than the first surface finish.

Example 5

The method of any one or more of Examples 1 through 4, wherein the at least one feature comprises a first distal cutout in the first side wall and a second distal cutout in the second side wall, wherein the first and second distal cutouts are configured to align a staple cartridge, wherein the at least one feature comprises a first distal cutout in the first side wall and a second distal cutout in the second side wall.

Example 6

The method of any one or more of Examples 1 through 5, wherein the at least one feature comprises a first proximal aperture in the first side wall and a second proximal aperture in the second side wall.

Example 7

The method of Example 6, wherein only distal portions of the first and second proximal apertures are machined such that the remainder of the first and second proximal apertures are not machined.

Example 8

The method of Example 6 or Example 7, wherein the near net shapes of the first and second proximal apertures have a first area, wherein the machined shapes of the first and second proximal apertures have a second area that is greater than the first area.

Example 9

The method of any one or more of Examples 1 through 8, wherein providing the lower jaw comprises forming the lower jaw to include the U-shaped body portion with first and second outwardly extending flanges, wherein the first outwardly extending flange extends from the first side wall and the second outwardly extending flange extends from the second side wall.

Example 10

The method of Example 9, wherein forming the lower jaw comprises a first stamping process to form the U-shaped body portion and the first and second outwardly extending flanges, wherein forming at least one feature includes a second subsequent stamping process to impart the at least one feature.

Example 11

The method of Example 9, wherein forming the lower jaw comprises forming the lower jaw using at least one of additive manufacturing, selective laser melting, direct metal laser sintering, or metal injection molding.

Example 12

The method of Example 9 or Example 10, wherein the method further comprises providing a flat body prior to forming the lower jaw to include a U-shaped body portion.

Example 13

The method of any one or more of Examples 9 through 12, further comprising removing the first and second outwardly extending flanges using at least one manufacturing process.

Example 14

The method of any one or more of Examples 9 through 13, wherein forming the lower jaw comprises stamping at least one aperture into the bottom wall.

Example 15

The method of any one or more of Examples 1 through 14, wherein after machining the at least one feature, the method further comprises coupling a lower longitudinally extending back to a bottom surface of the bottom wall.

Example 16

A method of manufacturing a lower jaw of an end effector of a surgical instrument, the method comprising: (a) stamping a lower jaw of an end effector of the surgical instrument to include a U-shaped body portion, wherein the U-shaped body portion includes a bottom wall and opposing first and second side walls; (b) stamping the first wall to includes a first proximal aperture, wherein the first proximal aperture has a near net shape with a first area; (c) stamping the second wall to include a second proximal aperture, wherein the second proximal aperture has a near net shape with the first area; and (d) subsequently machining the first and second proximal apertures to have machined shapes with second areas, wherein the second areas are greater than the first areas.

Example 17

The method of Example 16, subsequently machining only distal portions of the first and second proximal apertures such that the remainder of the first and second proximal apertures are not machined.

Example 18

An instrument, comprising: (a) a body; (b) a shaft extending from the body; and (c) an end effector in communication with the shaft, wherein the end effector is operable to compress, staple, and cut tissue, wherein the end effector includes a lower jaw, wherein the lower jaw comprises: (i) a bottom wall, (ii) a first side wall extending from the bottom wall, wherein the first side wall includes a first feature having a first machined shape produced by machining a first initial near net shape, and (iii) a second side wall extending from the bottom wall and disposed opposite the first side wall, wherein the second side wall includes a second feature having a second machined shape produced by machining a second initial near net shape.

Example 19

The instrument of Example 18, wherein the first feature includes a first proximal aperture and the second feature includes a second proximal aperture, wherein the first and second proximal apertures have machined shapes with machined areas that are greater than initial areas produced by the first and second initial near net shapes of the first and second proximal apertures.

Example 20

The instrument of Example 18 or Example 19, wherein the first feature includes a first distal cutout in the first side wall and the second feature includes a second distal cutout in the second side wall, wherein the first and second distal cutouts are configured to align a staple cartridge, wherein the machined shapes of the first and second distal cutouts produce 90-degree interior angles that are initially formed in the first and second initial near net shapes as obtuse interior angles using at least one stamping process.

Example 21

The instrument of any one or more of Examples 18 through 20, wherein at least one of the first and second features is formed using at least one stamping process.

Example 22

The instrument of any one or more of Examples 18 through 21, wherein the first feature is formed in the first side wall using a first manufacturing process, and the second feature is formed in the second side wall using a second manufacturing process.

Example 23

The instrument of any one or more of Examples 18 through 22, wherein non-machined portions of the lower jaw have a first surface finish and machined portions of the lower jaw have a second surface finish, wherein the second surface finish is finer than the first surface finish.

Example 24

The instrument of any one or more of Examples 18 through 19 and Examples 21 through 22, wherein the first feature includes a first distal cutout in the first side wall, wherein the second feature includes a second distal cutout in the second side wall, wherein the first and second distal cutouts are configured to align a staple cartridge, wherein the first and second initial near net shapes produce obtuse interior angles, wherein the first and second machined shapes produce 90-degree interior angles.

Example 25

The instrument of any one or more of Example 18 and Examples 20 through 24, wherein the first feature includes a first proximal aperture in the first side wall, wherein the second feature includes a second proximal aperture in the second side wall.

Example 26

The instrument of Example 19 or Example 25, wherein only distal portions of the first and second proximal apertures are machined such that the remainder of the first and second proximal apertures are not machined.

Example 27

The instrument of any one or more of Examples 18 through 26, wherein the first and second initial near net shapes have a first area, wherein the first and second machined shapes have a second area that is greater than the first area.

Example 28

The instrument of any one or more of Examples 18 through 27, wherein the lower jaw is formed through a first stamping process to form the U-shaped body portion and first and second outwardly extending flanges.

Example 29

The instrument of any one or more of Examples 18 through 28, wherein the lower jaw is formed using at least one of additive manufacturing, selective laser melting, direct metal laser sintering, or metal injection molding.

Example 30

The instrument of Example 28, wherein the first and second outwardly extending flanges are configured to be removed using at least one manufacturing process.

Example 31

The instrument of any one or more of Examples 18 through 30, wherein the lower jaw includes at least one aperture stamped into the bottom wall.

Example 32

The instrument of any one or more of Examples 18 through 31, wherein the instrument further comprises a lower longitudinally extending back coupled with a bottom surface of the bottom wall.

IV. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of manufacturing a lower jaw of an end effector of a surgical instrument, the method comprising:
   (a) forming a body portion of the lower jaw using at least one of stamping, additive manufacturing, selective laser melting, direct metal laser sintering, or metal injection molding, wherein the body portion includes a bottom wall interposed between first and second opposing side walls;
   (b) forming at least one feature into at least one of the first or second side walls; and
   (c) machining the at least one feature into at least one of the first or second side walls after forming the at least one feature.

2. The method of claim 1, wherein forming the body portion further comprises forming the body portion using additive manufacturing.

3. The method of claim 1, wherein forming the body portion further comprises forming the body portion using selective laser melting.

4. The method of claim 1, wherein forming the body portion further comprises forming the body portion using direct metal laser sintering.

5. The method of claim 1, wherein forming the body portion further comprises forming the body portion using metal injection molding.

6. The method of claim 1, wherein forming the body portion further comprises forming the body portion using one or more stamping processes.

7. The method of claim 1, wherein forming the at least one feature is performed while forming the body portion.

8. The method of claim 1, wherein forming the at least one feature is performed after forming the body portion.

9. The method of claim 1, wherein forming the at least one feature further comprises forming a first feature in the first side wall using a first manufacturing process, and subsequently forming a second feature in the second side wall using a second manufacturing process.

10. The method of claim 1, wherein non-machined portions of the body portion have a first surface finish and machined portions of the body portion have a second surface finish, wherein the second surface finish is finer than the first surface finish.

11. The method of claim 1, wherein the at least one feature comprises a first distal cutout in the first side wall and a second distal cutout in the second side wall, wherein the first and second distal cutouts are configured to align a staple cartridge, wherein the first and second distal cutouts have obtuse interior angles prior to machining the first and second distal cutouts, wherein the first and second distal cutouts have approximately 90-degree interior angles after machining the first and second distal cutouts.

12. The method of claim 11, wherein the first and second distal cutouts have a first area prior to machining the first and second distal cutouts, wherein the first and second distal cutouts have a second area after machining the first and second distal cutouts that is greater than the first area.

13. The method of claim 1, wherein forming the body portion further comprises forming at least one aperture into the bottom wall.

14. The method of claim 1, wherein the body portion has a U-shape.

15. A method of manufacturing a lower jaw of an end effector of a surgical instrument, the method comprising:
   (a) forming a body portion of the lower jaw of the end effector of the surgical instrument, wherein the body portion includes a bottom wall and opposing first and second side walls;
   (b) stamping the first side wall to include a first distal cutout, wherein the first distal cutout has a first area prior to machining;
   (c) stamping the second side wall to include a second distal cutout, wherein the second distal cutout has the first area prior to machining; and
   (d) subsequently machining the first and second distal cutouts to each have a second area that is greater than the first area.

16. The method of claim 15, wherein forming the body portion further comprises stamping the body portion using one or more stamping processes.

17. The method of claim 15, wherein forming the body portion comprises stamping at least one aperture into the bottom wall.

18. The method of claim 15, wherein the first and second distal cutouts are configured to align a staple cartridge, wherein the first and second distal cutouts have obtuse interior angles prior to machining the first and second distal cutouts, wherein the first and second distal cutouts have approximately 90-degree interior angles after machining the first and second distal cutouts.

19. An instrument, comprising:
   (a) a shaft extending distally; and
   (b) an end effector in communication with the shaft, wherein the end effector is operable to compress, staple, and cut tissue, wherein the end effector includes a lower jaw comprising:
      (i) a bottom wall,
      (ii) a first side wall extending from the bottom wall, wherein the first side wall includes a first feature having a first machined shape produced by machining a first initial shape, the first feature having a machined surface finish, and
      (iii) a second side wall extending from the bottom wall and disposed opposite the first side wall, wherein the second side wall includes a second feature having a second machined shape produced by machining a second initial shape.

20. The instrument of claim 19, wherein the first feature includes a first distal cutout in the first side wall, wherein the second feature includes a second distal cutout in the second side wall, wherein the first and second distal cutouts are configured to align a staple cartridge, wherein the first and second initial shapes have obtuse interior angles, wherein the first and second machined shapes have approximately 90-degree interior angles.

* * * * *